(12) United States Patent
Ziegler et al.

(10) Patent No.: US 7,986,411 B2
(45) Date of Patent: Jul. 26, 2011

(54) IMAGING OF A TURBID MEDIUM

(75) Inventors: Ronny Ziegler, Hamburg (DE); Tim Nielsen, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 28 days.

(21) Appl. No.: 12/518,891

(22) PCT Filed: Dec. 12, 2007

(86) PCT No.: PCT/IB2007/055043
§ 371 (c)(1),
(2), (4) Date: Jun. 12, 2009

(87) PCT Pub. No.: WO2008/075252
PCT Pub. Date: Jun. 26, 2008

(65) Prior Publication Data
US 2010/0014084 A1   Jan. 21, 2010

(30) Foreign Application Priority Data

Dec. 19, 2006 (EP) .................................... 06126442

(51) Int. Cl.
*G01N 21/00* (2006.01)
(52) U.S. Cl. ........ 356/433; 600/431; 600/109; 600/473; 356/408; 356/407
(58) Field of Classification Search .................. 356/433, 356/407, 432, 408; 600/431, 473–477, 109, 600/407, 408
See application file for complete search history.

(56) References Cited

U.S. PATENT DOCUMENTS

| 4,945,239 | A | 7/1990 | Wist | |
|---|---|---|---|---|
| 6,175,759 | B1 | 1/2001 | Chan | |
| 6,280,386 | B1 | 8/2001 | Alfano | |
| 6,687,532 | B2 * | 2/2004 | Ohmae et al. | 356/432 |
| 6,738,658 | B2 * | 5/2004 | Wake et al. | 600/407 |
| 2003/0135122 | A1 | 7/2003 | Bambot | |
| 2004/0245350 | A1 | 12/2004 | Zeng | |

FOREIGN PATENT DOCUMENTS

| WO | 9901749 A1 | 1/1999 |
|---|---|---|
| WO | 0153802 A2 | 7/2001 |

* cited by examiner

*Primary Examiner* — Gregory J Toatley
*Assistant Examiner* — Iyabo S Alli

(57) ABSTRACT

An imaging system for imaging of a turbid medium comprises a radiation source to illuminate an object to be imaged. A detection system detects radiation from the object and includes a separation module which separates and distinguishes radiation components having respective wavelength ranges. An analysis module forms a comparison of respective radiation components. An image dataset is reconstructed on the basis of the comparison of respective radiation components. The comparison may involve the ratio of the levels of the high-wavelength radiation component to the low-wavelength radiation component, the relative difference of the levels of high-wavelength radiation component to the detected radiation, and the relative difference of the levels of the high-wavelength radiation component to the low-wavelength radiation component.

7 Claims, 2 Drawing Sheets

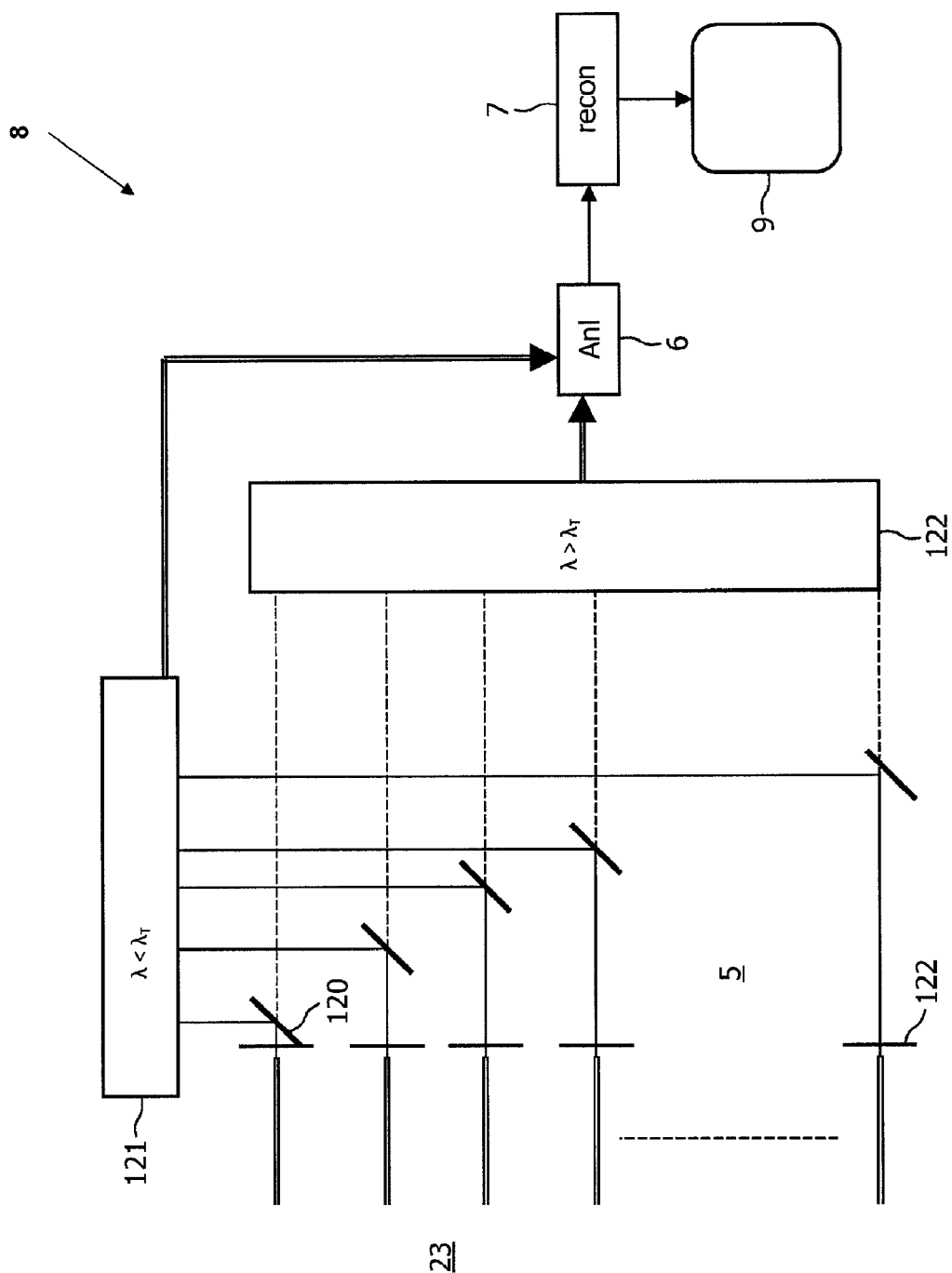

IMAGING OF A TURBID MEDIUM

FIELD OF THE INVENTION

The invention relates to an imaging system for imaging a turbid medium.

BACKGROUND OF THE INVENTION

An imaging system is known from the U.S. Pat. No. 6,738,658 in the form of a medical optical imaging scanner.

The known medical optical imaging scanner is notably arranged for breast imaging. An illumination source is positioned to direct light to the object to be imaged, i.e. the breast to be imaged. Light of different wavelength ranges emerging from the breast is simultaneously detected by respective groups of photodetectors. Optical filters are disposed in front of one of the groups of photodetectors to restrict the wavelength of light reaching that group of photodetectors.

Data from the filtered set of photodetectors are used to reconstruct a fluorescence image of the breast. Fluorescence is introduced in the breast through the use of a contrast agent in the form of a fluorophore which is excited by the illumination source. Data from the unfiltered set of photodetectors are used to reconstruct an absorption image of the breast. The fluorescent and absorption images of the breast are automatically co-registered within the perimeter of the breast. Subsequently, the absorption data are subtracted from the fluorescent data to reconstruct images that contain information that is new in the images obtained after application of the contrast agent.

SUMMARY OF THE INVENTION

An object of the invention is to provide an imaging system for imaging a turbid medium to improve contrast in the image independently of the concentration of contrast agent.

This object is achieved by an imaging system for imaging a turbid medium comprising
  a radiation source to illuminate an object to be imaged
  a detection system to detect radiation from the object and having a separation module which distinguishes radiation components having respective wavelength ranges
  an analysis module to form a comparison of respective radiation components and
  a reconstruction unit to access the comparison of respective radiation components and reconstruct an image dataset on the basis of the comparison of respective radiation components.

According to the invention the radiation components of different wavelength ranges are distinguished. The image is reconstructed on the basis of a comparison of these radiation components. An insight of the present invention is that the comparison of these radiation components avoids that contrast inversion occurs in the image caused by self-absorption of radiation propagating through the turbid medium. Another insight is that these radiation components can be distinguished on the basis of their respective wavelength ranges. Notably, good contrast in the reconstructed image is achieved when the comparison is relatively more beneficial to one of the wavelength ranges to the other ones over the relevant range of concentration of contrast agent. Accordingly, in the comparison competition among wavelength ranges is such that the intensity (or photon count) of that one wavelength range dominates so that any contrast in that one wavelength range does not suffer from contrast inversion.

The respective radiation components concern radiation that is propagated through the turbid medium and which have undergone predominantly strong or weak self-absorption, respectively e.g. by a fluorescent contrast agent. Notably, the respective radiation components concern radiation that has undergone strong or weak self-absorption by the contrast agent from the radiation source that is transmitted through the turbid medium and radiation that is generated due to excitation of a fluorescent contrast agent by the illumination source, respectively. The comparison of the fluorescent radiation from the object to the radiation component transmitted through the turbid medium of the object reduces the negative effect, notably inversion of contrast in the reconstructed image due to self-absorption of the fluorescent radiation.

There are several alternatives to distinguish the respective radiation components having respective wavelength ranges. One option is to employ optical filters, having respective pass-bands that correspond to the wavelength-ranges of the radiation components to be distinguished. Another option is to employ a dielectric mirror having reflection and transmission in the respective wavelength-ranges. Also, different sensitivity ranges for respective groups of detector elements may be employed so that respective detector groups detect mainly the respective radiation components. Alternatively, a spectrometer, a grating prism or an optical dispersion element may be employed to separate the respective different wavelength ranges.

These and other aspects of the invention will be further elaborated with reference to the embodiments defined in the dependent Claims.

According to one aspect of the invention, two radiation components are distinguished, i.e. the low-wavelength radiation components having wavelengths less than the ceiling wavelength and the high-wavelength radiation component having wavelengths above a threshold wavelength. In a practical implementation the ceiling wavelength and the threshold wavelength are equal. The high-wavelength radiation component mainly concerns fluorescent radiation that is generated by excitation of a fluorescent contrast agent and subsequently propagates through the turbid medium. It is noted that since the main processes during propagation are scattering and absorption, which are not much dependent on the energy of the near-infrared radiation, the energy distribution of the (e.g. near infrared) radiation is not changed as it propagates through the tissue. The low-wavelength radiation component concerns mainly radiation from the illumination source that is transmitted through the turbid medium and is partly absorbed in the turbid medium. The low-wavelength radiation component and the high-wavelength component further distinguish between the dominating of self-absorption and non-dominating of self-absorption of the fluorescent radiation. The comparison of the high-wavelength radiation component to the low-wavelength component effectively eliminates the effect of self-absorption in the turbid medium. Accordingly, the image that is reconstructed on the basis of the comparison has contrast that is an increasing function of the employed concentration of contrast agent. Notably, as contrast inversion is avoided, low contrast is avoided due to compensation of fluorescence by auto-absorption. Thus, the diagnostic quality of the image is improved in that details even at low contrast are not obscured by contrast inversion and remain well visible.

There are particular implementations of the comparison that lead to very good results in that contrast increases with concentration of contrast agent. Notably this is achieved by using the ratio of the levels of the high-wavelength radiation component to the low-wavelength radiation component. This ratio appears to be monotonously increasing with increasing concentration of contrast agent over at least one or two orders of magnitude. Another implementation is to base the reconstruction of the ratio of (i) the difference between the intensity levels of the high-wavelength radiation component and the low-wavelength radiation component to (ii) the intensity level of the high-wavelength radiation component. This relative ratio also appears to increase linearly with concentration of contrast agent over at least two orders of magnitude. Yet another version bases the reconstruction on the relative difference of the levels of the high-wavelength radiation component to the low-wavelength radiation component. In this version an about logarithmic increase with concentration of contrast agent over at least two orders of magnitude.

According to a further aspect of the invention the imaging system is provided with the option to base the reconstruction on the total level of detected radiation, i.e. the sum of the levels of the two (or more) radiation components. This option is notably activated when a low concentration of contrast agent is applied. At such low concentration of contrast agent self-absorption does not or only hardly occur so that contrast inversion is quite unlikely. On the other hand, the signal-to-noise ratio (SNR) of the total level of detected radiation is higher than the SNR of an individual radiation component. Hence to use the so-called full spectrum of the summed levels of all radiation components achieves a reconstructed image having a better SNR.

Further it is noted that the imaging system of the invention is in particular destined to image an object that is formed at least partly from a turbid medium through which the radiation propagates to a large extent by scattering. Inhomogeneities may be present in the turbid medium which influence the propagation of radiation. A particular example is biological tissue, such as a woman's breast. The imaging system of the invention is notably employed to image a woman's breast to reveal the presence of inhomogeneities such as benign or malignant tumors. For optical tomography of biological tissue, such as a woman's breast near-infrared radiation is particularly suitable because biological tissue is reasonably low absorbing but quite highly scattering in the wavelength range of 400 nm to 1400 nm, in particular good results are obtained in the wavelength range between 600 nm and 950 nm.

There are various ways to access the level of the respective radiation components. Depending on the detection technique employed the intensities or the signal amplitudes of the radiation components can be measured.

The invention also relates to an imaging method, in particular a digital optical tomography method. This optical imaging method of the invention achieves that in imaging of a turbid medium contrast inversion at increasing concentration of contrast agent is avoided. The invention further relates to a computer program. The computer program of the invention can be provided on a data carrier such as a CD-ROM disk, or the computer program of the invention can be downloaded from a data network such as the worldwide web. When installed in the computer included in a imaging system for imaging a turbid medium the imaging system is enabled to operate according to the invention and achieve better image quality in that contrast inversion is avoided.

BRIEF DESCRIPTION OF THE DRAWINGS

These and other aspects of the invention will be elucidated with reference to the embodiments described hereinafter and with reference to the accompanying drawing wherein.

DETAILED DESCRIPTION OF THE PREFERRED EMBODIMENTS

Figure 1:
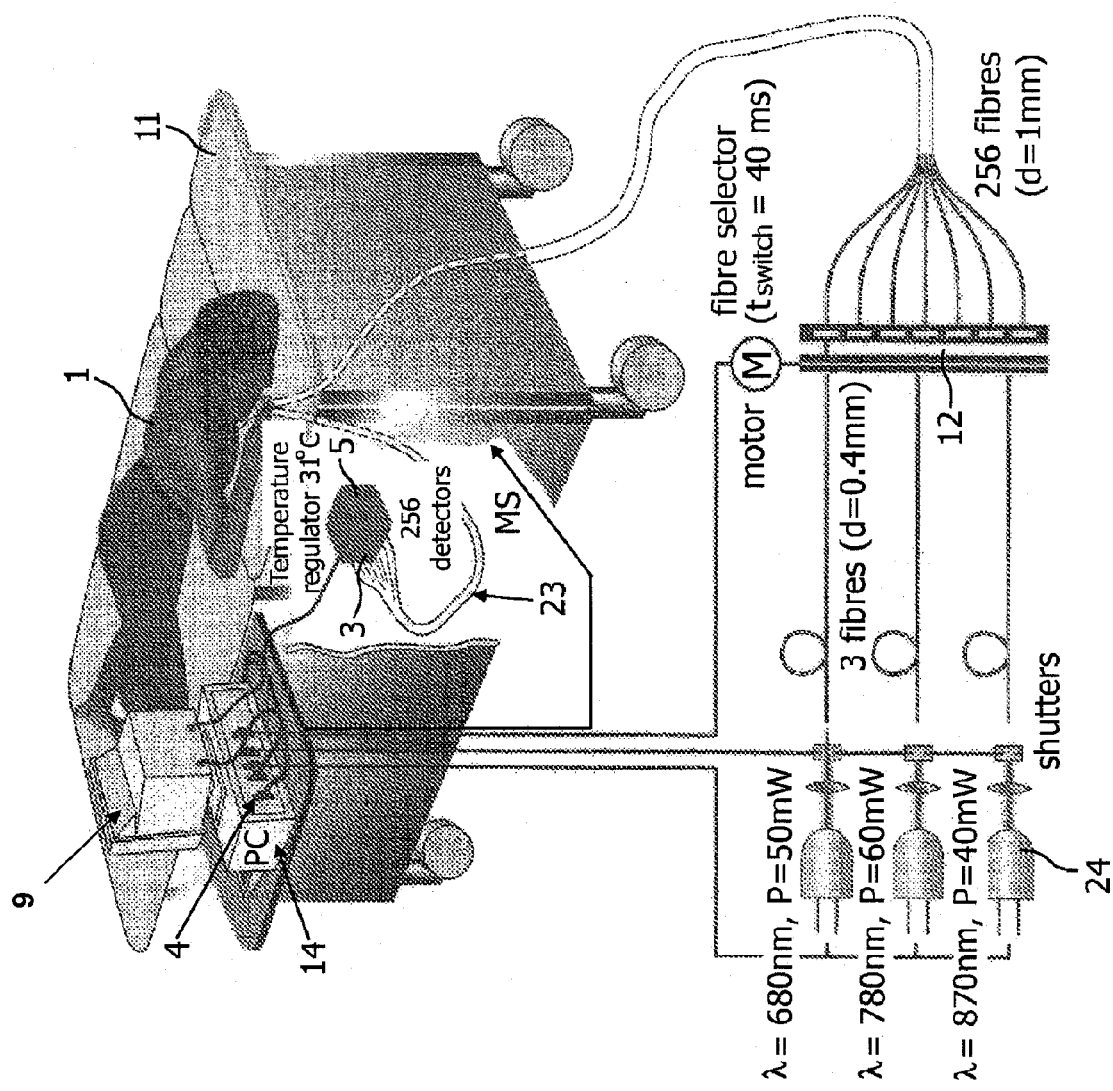
FIG. 1 shows a schematic diagram of the system for imaging a turbid medium of the invention and FIG. 2 schematically shows further details of an example of the detector module of the imaging system of the invention.

FIG. 1 shows a schematic diagram of the system for imaging a turbid medium of the invention. Notably, the imaging system of FIG. 1 is a digital optical tomography system that is capable of producing an image of the interior of the object to be imaged. Notably, the system for imaging a turbid medium shown diagrammatically in FIG. 1 is an optical mammography system. The optical mammography system comprises a carrier 11, e.g. having the form of a patient bed or patient table, on which the patient to be examined (notably a woman whose breast(s) 1 are to be examined) is placed in prone position (i.e. face down) having one breast suspended in the examination space 2 that has the form of a measurement cup (not visible in FIG. 1). The measurement cup is further filled with a matching liquid that has optical scattering and absorption properties that closely resemble the optical scattering and absorption properties of the woman's breast.

A large number of fibers 23 (e.g. 510 in total) is connected with one end to the measurement cup. Half of the fibers are connected to detector modules 5 with an other end 3, and half of the fibers are connected to a fiber-switch 12 through a further end. The fiber-switch 12 can direct light from three different lasers 24 in either one of the 256 source fibers 23 (255 to the measurement cup, one directly to a detector fiber). In this way, either one of the source fibers 23 can provide a conical light beam in the measurement cup. By properly switching the fiber-switch 12, all the source fibers will emit a conical light beam into the breast tissue subsequently.

The light from the selected source fiber is scattered by the matching fluid and the breast, and is detected by the 255 detector modules. When a fluorescent contrast agent is employed the light from the source fiber excites the fluorescent contrast agent to emit fluorescent light at a (slightly) longer wavelength. The detector modules are arranged to also detect the fluorescent and transmitted light from the patient to be examined, notably the woman's breast. The detector fibers are often arranged to arrive at detection position in respective rings around the wall of the measurement cup. The rings are displaced along the long axis (usually vertical) of the measurement cup. The attenuation of light in breast tissue is strong, which means that only a limited amount of photons can transverse the breast, compared to the reflected (or back-scattered) light. Therefore, a large dynamical range should be covered by the detectors (about nine orders of magnitude). Photodiodes are used as photosensors 5 in the detector modules. The front-end detector electronics includes one of these photodiodes and an amplifier. The amplification factor of the amplifier can be switched between several values. The machine first measures at the lowest amplification, and increases the amplification if necessary. The detectors are controlled by a computer 14.

The computer 14 including a display 9 also controls the lasers, the fiber-switch, and the fluid dispensing system through connectors 4. The computer, measurement cup, fibers, detectors, fiber-switch, and the lasers are all mounted into a bed as shown in FIG. 1.

FIG. 2 schematically shows further details of an example of the detector module of the imaging system of the invention. The optical fibers 23 are optically coupled to input channels at the input side of a detector module 8. The detector module 8 is provided with a separation module in the form of dielectric mirrors 120 for the respective input channels. Each of dielectric mirrors is substantially reflective for the low-wavelength component and substantially transmitting for the high-wavelength component. These dielectric mirrors are such as optical components commercially available. Light having a wavelength less than the threshold wavelength is reflected and light that has a wavelength larger than the threshold wavelength is transmitted. For example when as a contrast agent the NIR96010 (SIDAG) dye is employed, laser excitation may be performed at a wavelength of 740 nm and fluorescence emission occurs in the range of wavelengths if 760 nm to 850 nm. Good results are obtained by setting the threshold and ceiling wavelength in the range between 780 nm and 790 nm. The reflected low-wavelength component is reflected towards a high-energy detection sub-module 121 which includes photosensors that are sensitive for the low-wavelength component. In practice, the high-energy detection sub-module and the low-energy sub-module are equipped with the same or similar type photosensors having an intrinsic sensitivity range that covers both the high-wavelength and the low-wavelength ranges and to provide the high-energy and low-energy sub-module with different optical input filters. There optical input filters have pass bands for the low-wavelength and high-wavelength ranges, respectively. The laser 23 to excite the contrast agent (aprrox. 690 nm for SIDAG) is filtered at pre-filters 122. This pre-filtering avoids that the signal from the excitation laser 23 dominates the fluorescence signal. This pre-filter 122 in this example filters all wavelengths smaller than approx. 750 nm. The remaining spectrum is produced by the contrast agent, and this one again is split into lower and upper wavelength ranges to separate the self-absorption dominated ($\lambda<\lambda_T$) from non-dominated region ($\lambda>\lambda_T$), where $\lambda_T$ is the threshold wavelength.

The transmitted high-wavelength component is transmitted to a low-energy detection sub-module 122 which includes photosensors that are sensitive for the high-wavelength component. The dielectric mirrors are e.g. suitably coated to achieve the required wavelength reflection and transmission. The high-energy detection sub-module outputs an electronic output signal that represents a spatially resolved distribution of the intensities of the low-wavelength radiation component from the object to be imaged. The low-energy detection sub-module outputs an electronic output signal that represents a spatially resolved distribution of the intensities of the high-wavelength radiation component from the object to be imaged. The electric output signals of the respective detection sub-modules are applied to the analysis module 6 which performs a comparison. The comparison between the low-wavelength component and the high-wavelength component is e.g. simply performed by computing its ratio. It appears that notably this ratio is more in favor to the low-wavelength component over a wide range of concentrations of the fluorescent contrast agent. The comparison made by the analysis module is applied to the reconstruction module 7. For example, the analysis module provides the ratio of the low-wavelength component to the high-wavelength component for a large number of respective pairs of source and detection positions. These individual detection positions are in fact the positions of the fiber tips of the detection fibers at the surface of the object to be imaged. These positions are relative to the object e.g. the woman's breast. The source position is in fact the position (relative to the object) of the fiber that is selected to apply the laser light to the object, e.g. the woman's breast. From the comparison the reconstruction module reconstructs the image of the interior of the object to be imaged on the display 9. This reconstruction notably involves an algebraic reconstruction, a back-transformation or a Rytov approximation may be employed.

The invention claimed is:

1. An imaging system for imaging of a turbid medium comprising:
    a radiation source to illuminate an object to be imaged;
    a detection system to detect a plurality of distinct radiation portions from the object and having a separation module which separates each of the plurality of distinct radiation portions into a respective first radiation component having a wavelength less than a threshold wavelength and a respective second radiation component having a wavelength larger than the threshold wavelength;
    an analysis module to form a comparison of respective first and second radiation components; and
    a reconstruction unit to access the comparison of respective first and second radiation components and reconstruct an image dataset on the basis of the comparison of the respective first and second radiation components.

2. The imaging system as claimed in claim 1, wherein the separation module comprises a respective dielectric mirror for each one of the plurality of distinct radiation portions that is substantially reflective for the wavelength less than the threshold wavelength and substantially transmitting for the wavelength larger than the threshold wavelength.

3. The imaging system as claimed in claim 2, wherein
    the analysis module is arranged to form the comparison from the low-wavelength radiation component and the high-wavelength component
    in the form of the ratio of the levels of the wavelength larger than the threshold wavelength radiation component to the wavelength less than the threshold wavelength radiation component, or
    in the form of the relative difference of the levels of wavelength larger than the threshold wavelength radiation component to a total of detected radiation, or
    in the form of the relative difference of the levels of the wavelength larger than the threshold wavelength radiation component to the wavelength less than the threshold wavelength radiation component.

4. The imaging system as claimed in claim 2, wherein
    the reconstruction module is arranged to access a total level of detected radiation and is provided with an option to reconstruct the image on a basis of the total level of detected radiation.

5. The imaging system as claimed in claim 4, wherein
    a control unit is provided to activate the option to reconstruct the image on the basis of the tota level of detected radiation in dependence of an applied concentration of contrast agent.

6. A method of imaging of a turbid medium comprising acts of:
    illuminating of an object to be imaged;
    detecting radiation from the object using a detecting device that separates each of a plurality of distinct radiation portions into a respective first radiation component having a wavelength less than a threshold wavelength and a respective second radiation component having a wavelength larger than the threshold wavelength;
    forming a comparison of respective first and second radiation components; and
    reconstruction from the comparison of respective first and second radiation components an image dataset on the basis of the comparison of respective first and second radiation components.

7. A computer program stored on a computer readable non-transitory memory medium, the program including instructions for performing acts of:

detecting radiation from the object using a detecting device that separates each of a plurality of distinct radiation portions into a respective first radiation component having a wavelength less than a threshold wavelength and a respective second radiation component having a wavelength larger than the threshold wavelength;

forming a comparison of respective first and second radiation components; and reconstruction from the comparison of respective first and second radiation components an image dataset.

* * * * *